(12) United States Patent
Ljunggreen et al.

(10) Patent No.: US 6,585,699 B2
(45) Date of Patent: Jul. 1, 2003

(54) DRUG DELIVERY DEVICE PROVIDED WITH A ONE-WAY MECHANISM

(75) Inventors: Henrik Ljunggreen, Ballerup (DK); Jens Ulrik Poulsen, Virum (DK); Soren Aasmul, Holte (DK); Lars Hofmann Christensen, Jyllinge (DK); Jens Moller-Jensen, Copenhagen (DK); Peter Moller-Jensen, Copenhagen (DK)

(73) Assignee: NNA/S, Bagsvaerd (DK)

( * ) Notice: Subject to any disclaimer, the term of this patent is extended or adjusted under 35 U.S.C. 154(b) by 6 days.

(21) Appl. No.: 09/822,162

(22) Filed: Mar. 30, 2001

(65) Prior Publication Data

US 2002/0004651 A1 Jan. 10, 2002

Related U.S. Application Data

(60) Provisional application No. 60/201,518, filed on May 2, 2000, and provisional application No. 60/207,808, filed on May 30, 2000.

(30) Foreign Application Priority Data

Apr. 13, 2000 (DK) .......................... 2000 00622

(51) Int. Cl.[7] .......................... A61M 5/28; A61M 5/315; A61M 5/00
(52) U.S. Cl. .......................... 604/207; 604/224; 604/246
(58) Field of Search ................................. 604/207, 209, 604/210, 211, 218, 220, 224, 246; 222/309, 325

(56) References Cited

U.S. PATENT DOCUMENTS

| | | | |
|---|---|---|---|
| 3,703,941 A | 11/1972 | Ohie et al. | 188/31 |
| 4,367,739 A * | 1/1983 | LeVeen et al. | 604/224 |
| 4,493,704 A | 1/1985 | Beard et al. | 604/154 |
| 4,820,287 A | 4/1989 | Leonard | 604/209 |
| 5,300,042 A | 4/1994 | Kossoff et al. | 604/210 |
| 5,630,339 A | 5/1997 | Tuday | |
| 6,003,736 A | 12/1999 | Ljunggreen | 222/309 |

FOREIGN PATENT DOCUMENTS

| | | | | |
|---|---|---|---|---|
| FR | 2 767 479 | 8/1997 | | A61M/5/20 |
| SE | 469 263 | 4/1991 | | A61M/5/315 |
| WO | WO 95/09021 | 9/1994 | | A61M/5/315 |
| WO | WO 96/26754 | 2/1996 | | A61M/5/315 |
| WO | WO 98/01173 | 6/1997 | | A61M/5/315 |
| WO | WO 98/10814 | 9/1997 | | A61M/5/24 |

* cited by examiner

Primary Examiner—Brian L. Casler
Assistant Examiner—Catherine Serke
(74) Attorney, Agent, or Firm—Marc A. Begam, Esq.; Richard W. Bork, Esq.; Reza Green, Esq.

(57) ABSTRACT

A drug delivery device comprising a housing (1) with a drug container (2) being provided with delivering means comprising a piston (5) for expelling a drug (4) from the drug container (2). The housing (1) further comprising a displaceable piston rod (6) abutting the piston (5) of the drug container (2) and rotating means being in engagement with the piston rod (6), said rotating means being provided with a one-way mechanism. The one-way mechanism comprises a helical spring (12) wound tightly around an axle (11), one end of said helical spring (12) being fixed in relation to the housing (1), the other end of the helical spring (12) being in a free state.

20 Claims, 1 Drawing Sheet

DRUG DELIVERY DEVICE PROVIDED WITH A ONE-WAY MECHANISM

CROSS REFERRENCE TO RELATED APPLICATIONS

This application claims the benefit of priority under 35 U.S.C. §119 of U.S. Provisional Application No. 60/207,808, filed May 30, 2000, U.S. Provisional Application No. 60/201,518 filed May 2, 2000 and Danish Application PA 2000 00622, filed Apr. 13, 2000.

BACKGROUND OF THE INVENTION

The invention relates to a drug delivery device comprising a housing with a drug container, said drug container having delivering means comprising a piston for expelling a drug from the drug container, said housing further comprising a displaceable piston rod abutting the piston of the drug container, rotating means being in engagement with the piston rod, said rotating means being provided with a one-way mechanism.

The delivery device may be of any type that delivers a liquefied drug to a person as an aerosol spray, an injection or a high-pressure jet. Preferably, however, the delivery device is an injection syringe that may be of a single-use type or a type having an exchangeable drug container or cartridge.

A drug delivery device of this kind is known from U.S. Pat. No. 4,367,739 that discloses a syringe provided with a threaded actuating rod with a piston that is arranged in a container or barrel containing the drug. The actuating rod is provided with a knurled knob at the end opposite the piston, said knurled knob being provided with a one-way mechanism. The one-way mechanism comprises a ratchet lock that may be released by manually disengaging a ratchet tooth from a ratchet wheel.

This type of one-way mechanisms is known in a number of appliances where movement in one direction is allowed while movement in an opposite direction is prevented. The movement may be linear or rotating.

Although widely used, manufacturing of a ratchet lock is relatively complicated since it comprises manufacturing of a ratchet tooth part and a ratchet wheel, each having matching teeth, and mounting each of these parts with cooperating parts of the device in which the ratchet lock is to be used. Finally, the cooperating parts are assembled.

SUMMARY OF THE INVENTION

It is an object of the present invention to provide a drug delivery device with a rotatable axle provided with a one-way mechanism that is structurally simpler than the previously known one-way mechanisms of the known devices.

This is achieved by providing the drug delivery device mentioned in the opening paragraph with a one-way mechanism that comprises a helical spring wound tightly around said axle, one end of said helical spring being fixed in relation to the housing, the other end of the helical spring being in a free state.

By arranging the one-way mechanism in this way a very simple and yet reliable one-way mechanism is provided. Further, the one-way mechanism is easy to build into a drug delivery device since it comprises very few parts.

The drug delivery device may be of a single-use type or a type having an exchangeable drug container or cartridge. If the drug delivery device is of the latter type, a release button is provided, said release button being able to displace the free end of the helical spring in a direction of unwinding the helical spring. Thereby the helical spring loses its frictional engagement with the axle and the axle is free to rotate in either direction.

In this way the piston rod can be retracted from the cartridge and the cartridge can be exchanged.

In a preferred embodiment the piston rod is provided with a toothing and is in engagement with a piston rod driving wheel provided with a complementary toothing, said piston rod driving wheel being mounted on said axle. In this embodiment, displacement of the piston rod is provided by rotating the axle, said rotation being provided by any known means, e.g. by a push button in engagement with the axle or by an electric motor.

In order to minimize the size of the drug delivery device the piston rod may be flexible and is positioned partly around the piston rod driving wheel. A guiding face may be provided in the housing, said flexible piston rod being positioned between said guiding face and said piston rod driving wheel.

BRIEF DESCRIPTION OF THE DRAWINGS

The invention will be described in detail in the following with reference to the drawings in which.

DETAILED DESCRIPTION OF THE INVENTION

Figure 1:
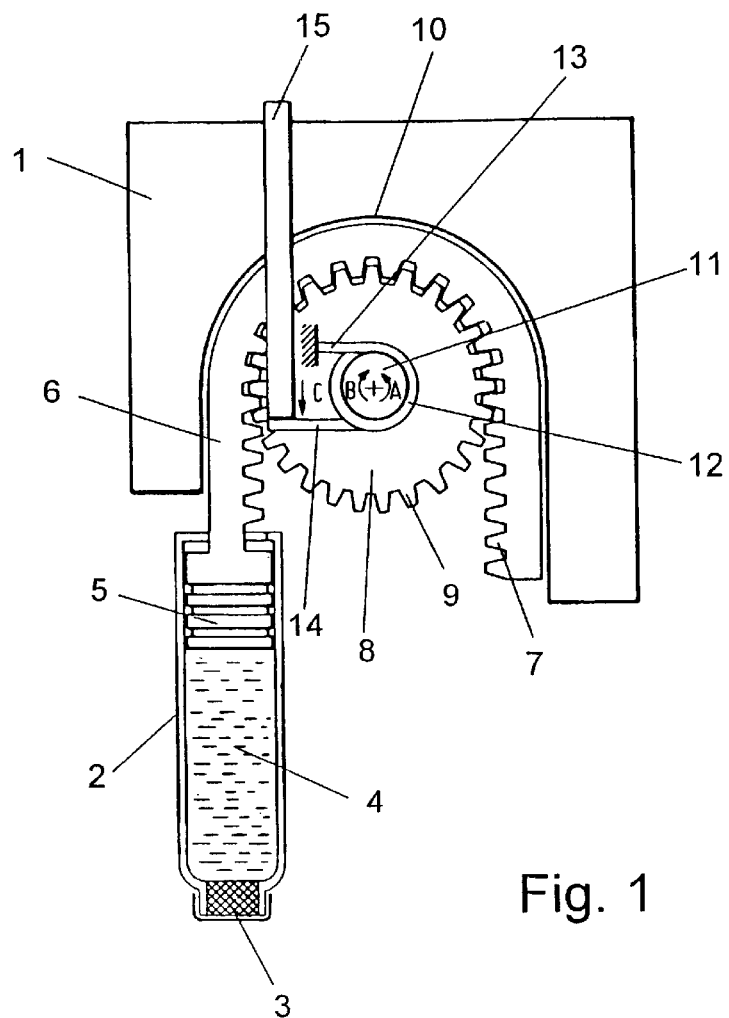
FIG. 1 shows a part of drug delivery device comprising a one-way mechanism according to the invention.

In FIG. 1 a part of a drug delivery device according to the invention is shown. The drug delivery device comprises a housing 1 provided with an accommodation for an exchangeable drug container or cartridge 2. The cartridge 2 is provided with a rubber seal 3 in a first end thereof, said rubber seal 3 being penetratable by a hollow injection needle (not shown) for administration of the drug 4 from the cartridge 2. A displaceable piston 5 is provided in the cartridge 2 for expelling the drug 4.

A flexible piston rod 6 is provided in the housing 1. One end of the flexible piston rod 6 abuts the piston 5 provided in the cartridge 2 and by displacing the flexible piston rod 6 the piston 5 is displaced in the cartridge 2, expelling an amount of the drug 4 from the cartridge 2.

The flexible piston rod 6 is provided with teeth 7 forming a toothing at the inwardly bending side and is in engagement with a piston rod driving wheel 8 provided with teeth 9 that are complementary with the teeth 7. The flexible piston rod 6 is positioned between the piston rod driving wheel 8 and a guiding face 10 of the housing 1.

The piston rod driving wheel 8 is mounted on an axle 11 which is rotatable in an anticlockwise direction (in the direction of the arrow A) as well as in a clockwise direction (in direction of the arrow B).

When the axle 11 is rotated in the direction of the arrow A, the flexible piston rod 6 is displaced downwards in the cartridge 2 displacing the piston 5 and expelling an amount of the drug 4. The axle 11 is rotated in the direction of the arrow A when an amount of the drug 4 is to be administrated to a person.

When the axle 11 is rotated in the direction of the arrow B, the flexible piston rod 6 is displaced upwards in the cartridge 2, optionally totally retracted from the cartridge 2. The axle 11 is rotated in the direction of the arrow B when the cartridge 2 is to be exchanged which requires that the flexible piston rod 6 is removed from the cartridge 2.

The rotation of the axle 11, which controls the displacement of the flexible piston rod 6, is controlled by any known means and is not shown. For instance, the axle 11 may be rotated by mechanical means, such as a push-button provided with a toothed rack that cooperates with a gearwheel provided on the axle 11, or it may be rotated by an electric motor. In the drug delivery device the dose to be administrated may be preset and administration is achieved either by pressing the push-button or by activating the electric motor whichever is the case.

In a drug delivery device it is important to prevent dose built-up, i.e. to assure that the amount of drug expelled from the cartridge 2 corresponds to the set dose when the axle 11 is rotated a preset rotation. Therefore, it is important that the flexible piston rod 6 in normal use is prevented from being displaced backwards in the cartridge 2. If the flexible piston rod 6 is displaced backwards in the cartridge 2 and no longer abuts the piston 5, the next amount of administrated drug will be smaller than prescribed which is undesirable.

In order to prevent the flexible piston rod 6 in being displaced backwards a helical spring 12 is wound tightly around the axle 11. The helical spring 12 has a first end 13 that is fixed to the housing 1 of the drug delivery device and a second end 14 that is in a free state inside the housing 1.

The helical spring 12 is wound tightly around the axle 11 and is therefore frictionally engaged with the axle 11. However, when the axle 11 is rotated anticlockwise in direction of the arrow A, the helical spring 12 loosens due to its free second end 14 and allows the axle 11 to be rotated in this direction.

If it is attempted to rotate the axle 11 clockwise in direction of the arrow B, the helical spring 12 is tightened even more due to the fixed first end 13 and the axle 11 is instantly prevented from being rotated in this direction.

The helical spring 12 being wound tightly around the axle 11 in this way assures that the axle 11 can be rotated in one direction only.

However, when the cartridge 2 is to be exchanged, the flexible piston rod 6 have to be retracted from the cartridge 2, i.e. it has to be drawn backwards by rotating the piston rod driving wheel 8 clockwise. As described above, this rotation is prevented by the helical spring 12 wound around the axle 11. However, by pressing the free end 14 of the helical spring 12 downwards in direction of the arrow C the helical spring 12 loses its frictional engagement with the axle 11 and the axle 11 is allowed to rotate clockwise thereby retracting the flexible piston rod 6 from the cartridge 2. The free end 14 of the helical spring 12 may be pressed downwards by a push-button 15 extending out of the hosing 1.

Figure 2:
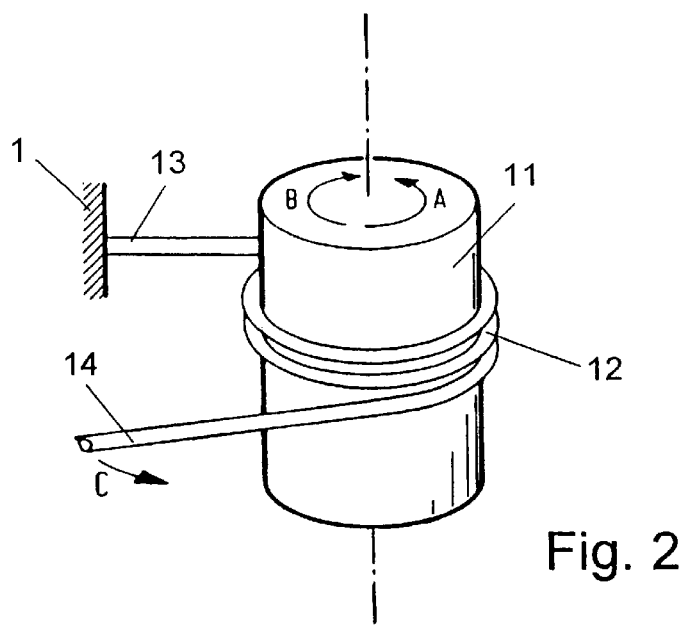
FIG. 2 shows in enlarged scale the working principle of the one-way mechanism.

The working principle of the above-described one-way mechanism is shown in FIG. 2 in an enlarged scale. The axle 11 is rotatable in an anticlockwise direction (arrow A) and in a clockwise direction (arrow B).

A helical spring 12 is wound tightly around the axle 11 thereby being in frictional engagement with the axle 11. A first end 13 of the helical spring 12 is fixed to the housing 1 of the drug delivery device while the other end 14 of the helical spring 12 is in a free state.

Rotation of the axle 11 in the direction of the arrow A is allowed since rotation in this direction loosens the helical spring 12 whereby the frictional engagement between the axle 11 and the helical spring 12 decreases.

Rotation of the axle 11 in the direction of the arrow B, however, is prevented since the frictional forces between the axle 11 and the helical spring 12 is increased instantly due to the ever more tightening of the helical spring 12.

If the free end 14 of the helical spring 12 is displaced in the direction of the arrow C, the helical spring is slightly unwound which causes the frictional engagement between the axle 11 and the helical spring 12 to decrease drastically and allows the axle 11 to be rotated clockwise.

The helical spring 12 is pre-wound before it is positioned on the axle 11. The pre-wound helical spring 12 preferably has an inner diameter that is slightly smaller than the outer diameter of the axle 11 when it is not mounted on the axle 11. When mounting the helical spring 12, it is slightly opened causing the inner diameter to increase to a size larger than the outer diameter of the axle 11. Then the helical spring 12 is positioned around the axle and released. When mounted, the helical spring 12 is in frictional engagement with the axle 11.

The invention has been described with reference to a preferred embodiment comprising a flexible piston rod 6. However, the invention may also be applied in other drug delivery devices where a rotating one-way mechanism is applicable.

What is claimed is:

1. A drug delivery device comprising:
a housing with a drug container, the drug container having a delivering means comprising a piston for expelling a drug from the container, the housing further comprising a displaceable piston rod abutting the piston of the drug container, a rotating means being in engagement with the piston rod, the rotating means being provided with a one-way mechanism,
wherein the one-way mechanism comprises a helical spring wound around an axle, the spring having one end of the spring being fixed in relation to the housing and a second end, and
the drug delivery device further comprising a release button that is able to displace the second end of the helical spring in a direction unwinding the helical spring.

2. A drug delivery device according to claim 1, wherein the piston rod is provided with a toothing and is in engagement with a piston rod drive wheel provided with a complementary toothing, the piston rod drive wheel being mount on an axle.

3. A drug delivery device according to claim 2, wherein the piston rod is flexible and is position partly around the piston rod drive wheel.

4. A drug delivery device according to claim 3, wherein a guiding face is provided in the housing, the flexible piston rod being position between the guiding face and the piston rod drive wheel.

5. A drug delivery device according to claim 1 wherein the drug delivery device is provide with an exchangeable drug container.

6. A drug delivery device according to claim 1, wherein the drug delivery device is an injection syringe.

7. A drug deliver device comprising:
a. a drug container having a piston
b. a housing;
c. a piston rod, at least a portion of which is linearly displaceable, the piston rod abutting the drug container piston;
d. a rotateable element coupled to the piston rod so that linear displacement of the piston rod in a first direction cause rotation of the element in a corresponding first direction and linear displacement of the piston rod in a second direction causes rotation of the element in a corresponding second direction;

e. a ratchetless means for substantially restricting rotation of the rotateable element in the corresponding first direction while allowing rotation in the corresponding second direction, thereby restricting linear displacement of the piston rod in the first direction but allowing linear displacement in the second direction.

8. The drug delivery device of claim 7, further comprising a release for releasing the ratchless means thereby allowing rotation of the rotateable element in two directions.

9. The drug delivery device of claim 7, wherein the ratchetless means comprises a spring, comprises a helically wound spring.

10. The drug delivery device of claim 7, wherein the ratchetless means is coupled to the rotateable element via a frictional force between the ratchless means and the rotateable element.

11. The drug delivery device of claim 10, wherein the rotateable element is a piston rod drive wheel.

12. A drug delivery device comprising:

a. a piston rod, at least a portion of which is linearly displaceable;

b. a rotateable element coupled to the piston rod so that rotation of the element in a first direction causes corresponding movement of the piston rod in a corresponding first direction and rotation of the element in a second direction causes movement of the piston rod in a corresponding second direction;

c. an axle fixed to the rotateable element, the axle having a cylindrical shape and an outside diameter;

d. a wound spring having an inside surface having a diameter, the diameter of the inside surface in a relaxed state that being smaller than the outside diameter of the axle, the spring having a first end fixed to the housing and a second that is free to move relative to the axle, the spring being rotatably coupled to the axle by a frictional force between the axle and the spring's inside surface, and e. wherein the spring is orientated with respect to its winding so that the frictional coupling force between the axle and the spring's inner surface increases to a level sufficient to prevent substantial rotation of the axle in the first direction when a force is applied to the rotateable element to rotate it in the first direction, thereby substantially preventing rotation of the rotateable element in the first direction and linear displacement of the piston rod in the corresponding first direction.

13. The drug delivery device of claim 12, wherein the spring is a helical spring.

14. The drug delivery device of claim 12, further comprising a means for partially unwinding the spring without rotating the axle.

15. The drug delivery device of claim 13, further comprising a means for partially unwinding the spring without rotating the axle.

16. The drug delivery device of claim 12, wherein the rotateable element rotates about an axis that is perpendicular to at least a portion of the piston rod.

17. The drug delivery device of claim 12, further comprising a cartridge containing an injectable medication, the cartridge having a first end that is covered with a pierceable membrane and a moveable piston and a medication holding space located therebetween, the piston abutting the piston rod.

18. The drug delivery device of claim 12, further comprising a release means for partially unwinding the spring.

19. The drug delivery device of claim 14, wherein the piston rod is a flexible piston rod.

20. The drug delivery device of claim 18, wherein the release is a button that abuts the second end of the spring.

* * * * *